US005741776A

United States Patent [19]

Clark et al.

[11] Patent Number: 5,741,776
[45] Date of Patent: *Apr. 21, 1998

[54] METHOD OF ADMINISTRATION OF IGF-I

[75] Inventors: Ross G. Clark, Pacifica; Neil Gesundheit, Palo Alto, both of Calif.; Marc R. Hammerman; Steven B. Miller, both of St. Louis, Mo.

[73] Assignees: Genentech, Inc., South San Francisco, Calif.; Washington University, St. Louis, Mo.

[*] Notice: The term of this patent shall not extend beyond the expiration date of Pat. No. 5,565,428.

[21] Appl. No.: 445,805

[22] Filed: May 22, 1995

[51] Int. Cl.$^6$ ............................ A61K 38/00; A61K 38/27
[52] U.S. Cl. .................................. 514/12; 514/4; 514/21
[58] Field of Search ..................... 514/12, 21, 4

[56] References Cited

U.S. PATENT DOCUMENTS

| | | | |
|---|---|---|---|
| 4,876,242 | 10/1989 | Applebaum | 514/12 |
| 4,988,675 | 1/1991 | Froesch et al. | 514/12 |
| 5,068,224 | 11/1991 | Fryklund et al. | 514/12 |
| 5,093,317 | 3/1992 | Lewis et al. | 514/12 |
| 5,106,832 | 4/1992 | Froesch et al. | 514/12 |
| 5,126,324 | 6/1992 | Clark et al. | 514/12 |
| 5,187,151 | 2/1993 | Clark et al. | 514/12 |
| 5,202,119 | 4/1993 | Clark et al. | 514/12 |
| 5,273,961 | 12/1993 | Clark | 514/12 |
| 5,374,620 | 12/1994 | Clark et al. | 514/12 |
| 5,565,428 | 10/1996 | Clark et al. | 514/12 |

FOREIGN PATENT DOCUMENTS

| | | |
|---|---|---|
| 327503 | 8/1989 | European Pat. Off. |
| WO 91/03253 | 3/1991 | WIPO |
| WO 91/18621 | 12/1991 | WIPO |
| WO 92/11865 | 7/1992 | WIPO |
| WO 92/13556 | 8/1992 | WIPO |
| WO 93/00109 | 1/1993 | WIPO |
| WO 93/00110 | 1/1993 | WIPO |
| WO 93/23071 | 11/1993 | WIPO |
| WO 93/25219 | 12/1993 | WIPO |
| WO 94/04030 | 3/1994 | WIPO |
| WO 94/09813 | 5/1994 | WIPO |
| WO 94/16722 | 8/1994 | WIPO |
| WO 95/08567 | 3/1995 | WIPO |
| WO 95/13824 | 5/1995 | WIPO |
| WO 95/28174 | 10/1995 | WIPO |

OTHER PUBLICATIONS

Baxter, "The somatomedins: insulin–like growth factors" *Advances in Clinical Chemistry* 25:49–115 (1986).

Binoux, M., "Donnees recentes sur les somatomedines" *Annales d'Endocrinologie* 41:157–191 (1980).

Chen et al., "Recombinant human IGF–I infusion results in transient improvement in nitrogen balance: evidence for IGF–I autoregulation" *US Endocrine Meeting* (Abstract 1596) p. 449 (1993).

Clemmons and Van Wyk, "Somatomedin: physiological control and effects on cell proliferation" *Handbook Exp. Pharmacol.* 57:161–208 (1981).

Cohick and Clemmons, "The insulin–like growth factors" *Annu. Rev. Physiol.* 55:131–153 (1993).

Duerr et al., "Insulin–like growth factor–1 enhances ventricular hypertrophy and function during the onset of experimental cardiac failure" *J. Clin. Invest.* 95:619–627 (1995).

Elahi et al., "Hemodynamic and metabolic responses to human insulin–like growth factor I (IGF–I) in men" *Modrn Concepts of Insulin–Like Growth Factors*, Spenser, ed., New York:Elsevier Science Publ. Co. pp. 219–224 (1991).

Guler et al., "Effects of recombinant insulin–like growth factor I on insulin secretion and renal function in normal human subjects" *Proc. Natl. Acad. Sci. USA* 86:2868–2872 (Apr. 1989).

Guler et al., "Insulin–like growth factor I increases glomerular filtration rate and renal plasma flow in man" *Acta Endocrinologica* 121:101–106 (1989).

Guler et al., "Recombinant human insulin–like growth factor 1 stimulates growth and has distinct effects on organ size in hypophysectomized rats" *Proc. Natl. Acad. Sci. USA* 85:4889–4893 (1988).

Guler et al., "Short–term metabolic effects of recombinant human insulin–like growth factor I in healthy adults" *New Egland J. of Medicine* 317(3):137–140 (1987).

Hammerman, "Ask the expert: What are the clinical uses of IGF I in acute and chronic renal failure?" *Ped. Nephrology* 8:544 (1994).

Hammerman and Miller, "The growth hormone insulin–like factor axis in kidney revisited" *Am. J. Physiol.* 265:F1–F14 (1993).

Hammerman and Miller, "Therapeutic use of growth factors in renal failure" *J. Am. Soc. Nephrol.* 5:1–11 (1994).

Hirschberg et al., "Effects of insulin–like growth factor I on renal function in normal men" *Kidney International* 43:387–397 (1993).

Hise et al., "Influence of circulating insulin–like growth factor–I compared with that of intrarenal insulin–like growth factor–I on proximal nephron receptor density in rats" *Clinical Science* 83:233–239 (1992).

Hoogenberg et al., "Effect of growth hormone and insulin–like growth factor I on urinary albumin excretion: studies in acromegaly and growth hormone deficiency" *Acta Endrocrinologica* 129:151–157 (1993).

(List continued on next page.)

*Primary Examiner*—Robert J. Hill, Jr.
*Assistant Examiner*—P. Lynn Touzeau
*Attorney, Agent, or Firm*—Janet E. Hasak

[57] ABSTRACT

A method is disclosed that comprises administering insulin–like growth factor-I (IGF-I) to a mammal so as to sustain its biological activity in the mammal comprising administering a therapeutically effective amount of IGF-I to the mammal to provide an exposure to IGF-I for a period of time that stimulates the maximum biological response in the mammal, then discontinuing said administration for a period of time equal to or less than the time period used for administration, and repeating this pattern of administration and discontinuance of administration for a period as long as necessary to achieve or maintain the desired biological response in the mammal.

17 Claims, 8 Drawing Sheets

OTHER PUBLICATIONS

Ikkos et al., "Glomerular filtration rate and renal plasma flow in acromegaly" *Acta Endocrinologica* 21:226–236 (1956).

Jabri et al., "Adverse effects of recombinant human insulin–like growth factor I in obese insulin–resistant type II diabetic patients" *Diabetes* 43:369–374 (1994).

Kanety et al., "Long–term treatment of Laron type dwarfs with insulin–like growth factor–1 increases serum insulin–like growth factor–binding protein–3 in the absence of growth hormone activity" *Acta Endocrinologica* 128:144–149 (1993).

Kerr et al., "Effect of insulin–like growth factor–1 on the responses to and recognition of hypoglycemia in humans" *J. Clin. Invest.* 91:141–147 (1993).

Kupfer et al., "Enhancement of the anabolic effects of growth hormone and insulin–like growth factor I by use of both agents simultaneously" *J. Clin. Invest.* 91:391–396 (1993).

Lieberman et al., "Anabolic effects of recombinant insulin–like growth factor I in AIDS–associated cachexia" *US Endocrine Meeting* (Abstract 1664) p. 466 (1993).

Lieberman et al., "Anabolic effects of recombinant insulin–like growth factor–I in cachectic patients with the acquired immunodeficiency syndrome" *J. Clin. Endocrinol. and Metab.* 78(2):404–410 (1994).

Lieberman et al., "Effects of recombinant human insulin–like growth factor–I (rhIGF–I) on total and free IGF–I concentrations, IGF–binding proteins, and glycemic response in humans" *J. Clin. Endocrinol. and Metab.* 75(1):30–36 (1992).

Miller et al., "Effects of IGF–I on reneal function in end-stage chronic renal failure" *Kidney Int.* 46:201–207 (1994).

O'Shea and Layish, "Growth hormone and the kidney: a case presentation and review of the literature" *J. Am. Soc. Nephrol.* 3:157–161 (1992).

O'Shea et al., "Effects of IGF–I on renal function in patients with chronic renal failur" *Am. J. Physiol.* 264:F917–F922 (1993).

O'Shea et al., "Roles of growth hormone and growth factors in the pathogenesis and treatment of kidney disease" *Current Opinion in Neph. and Hypertension* 2:67–72 (1993).

Quigley and Baum, "Effects of growth hormone and insulin–like growth factor I on rabbit proximal convoluted tubule transport" *J. Clin. Invest.* 88:368–374 (1991).

Quin et al. *New England J. of Medicine* 323:1425–1426 (1990).

Rinderknecht and Humbel, "The amino acid sequence of human insulin–like growth factor I and its structural homology with proinsulin" *Journal of Biological Chemistry* 253(8):2769–2776 (1978).

Rinderknecht and Humbel, "Polypeptides with nonsuppressible insulin–like and cell–growth promoting activities in human serum: isolation, chemical charaterization, and some biological properties of forms I and II" *Proc. Natl. Acad. Sci USA* 73(7):2365–2369 (1976).

Schalch et al., "Short–term metabolic effects of recombinant human insulin–like growth factor I (rhIGF–I) in type II diabetes mellitus" *Modern Concepts of Insulin–Like Growth Factors*, Spencer, ed., New York:Elsevier Science Publ. Co. pp. 705–714 (1991).

Schoenle et al., "Recombinant human insulin–like growth factor I(rhIGF I) reduces hyperglycaemia in patients with extreme insulin resistance" *Diabetologia* 34:675–679 (1991).

Underwood et al., "Regulation of somatomedin–c/insulin–like growth factor I by nutrients" *Hormone Res.* 24:166–176 (1986).

Usala et al., "Brief report: treatment of insulin–resistant diabetic ketoacidosis with insulin–like growth factor I in an adolescent with insulin–dependent diabetes" *New England J. of Medicine* 327(12):853–857 (1992).

Van Wyk et al., "The somatomedins: a family of insulinlike hormones under growth hormone control" *Recent Prog. Horm. Res.* 30:259–318 (1974).

Walker et al., "Stimulation of statural growth by recombinant insulin–like growth factor I in a child with growth hormone insensitivity syndrome (Laron type)" *J. Pediatr.* 121:641–646 (1992).

Wilton et al., "Treatment with recombinant human insulin–like growth factor I of children with growth hormone receptor deficiency (Laron syndrome)" *Acta Paediatr Suppl* 383:137–141 (1992).

Zenobi et al., "Effects of insulin–like growth factor–I on glucose tolerance, insulin levels, and insulin secretion" *J. Clin. Invest.* 89:1908–1913 (1992).

Zenobi et al., "Insulin–like growth factor–I improves glucose lipid metabolism in type 2 diabetes mellitus" *J. Clin. Invest.* 90:2234–2241 (1992).

*The Merck Index* (Abstract 887), Budavari, et al., Eleventh edition, Rahway, NJ:Merck & Co., Inc. pp. 137–138 (1989).

*The Merck Index* (Abstract only), Budavari, et al., Eleventh edition, Rahway, NJ:Merck & Co., Inc. pp. 267–268 (1989).

Jin et al., "Beneficial Effects of Growth Hormone and Insulin–like Growth Factor–1 in Experimental Heart Failure in Rats Treated with Chronic ACE Inhibition" *Journal of Cardiovascular Pharmacology* 26(3):420–425 (1995).

Webb et al., "The Endothelin Receptor Antagonist, BQ–123, Inhibits Angiotensin II–induced Contractions in Rabbit Aorta" *Biomedical and Biophysical Research Communications* 185(3):887–892 (Jun. 30, 1992).

(NORMAL=135-449 ng/ml)

(NORMAL=1.9-3.6 mg/L)

METHOD OF ADMINISTRATION OF IGF-I

This invention was made with government support under grant DK 27600 awarded by the National Institutes of Health. The government has certain rights in the invention.

BACKGROUND OF THE INVENTION

1. Field of the Invention

This invention relates to a method of dosing and administering IGF-I in an intermittent fashion such that the maximum favorable biological activity of IGF-I is achieved and maintained in the treatment of chronic disorders, with minimized unfavorable side effects.

2. Description of Related Disclosures

Human insulin-like growth factor-I (IGF-I) is a 7649-dalton polypeptide with a pI of 8.4 [Rinderknecht and Humbel, *Proc. Natl. Acad. Sci. USA*, 73:2365 (1976); Rinderknecht and Humbel, *J. Biol. Chem.*, 253: 2769 (1978)] belonging to a family of somatomedins with insulin-like and mitogenic biological activities that modulate the action of growth hormone (GH). Van Wyk et al., *Recent Prog. Horm. Res.*, 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986); U.S. Pat. No. 4,988,675; WO 91/03253; and WO 93/23071. IGF-I has hypoglycemic effects similar to insulin but also promotes positive nitrogen balance. Underwood et al., *Hormone Res.*, 24: 166 (1986); Guler et al., *N. Engl. J. Med.*, 317: 137 (1987). Due to this range of activities, IGF-I is being tested in humans for uses ranging from wound healing to the reversal of whole body catabolic states to treatment of heart conditions such as congestive heart failure. Guler et al., *Proc. Natl. Acad. Sci. USA*, 85: 4889 (1988); Duerr et al., *J. Clin. Invest.*, 95: 619–627 (1995). IGF-I is also being tested in the clinic for treating diabetes.

U.S. Pat. Nos. 5,273,961; 5,126,324; 5,187,151; 5,202,119; 5,374,620; 5,106,832; 4,988,675; 5,106,832; 5,068,224; 5,093,317; and 4,876,242 and WO 92/11865 and WO 94/16722 disclose various methods of treating patients using IGF-I.

A general scheme for the etiology of some clinical phenotypes which give rise to insulin resistance and the possible effects of administration of IGF-I on selected representative subjects is given in several references. See, e.g., Elahi et al., "Hemodynamic and metabolic responses to human insulin-like growth factor-1 (IGF-1) in men," in *Modern Concepts of Insulin-Like Growth Factors*, (Spencer, E M, ed.), Elsevier, New York, pp. 219–224 (1991); Quinn et al., *N. Engl. J. Med.*, 323: 1425–1426 (1990); Schalch et al., "Short-term metabolic effects of recombinant human insulin-like growth factor 1 (rhIGF-1) in type 11 diabetes mellitus," in: *Modern Concepts of Insulin-Like Growth Factors*, (Spencer, E M, ed.), Elsevier, New York, pp. 705–714 (1991); Schoenle et al.. *Diabetologia*, 34: 675–679 (1991); Usala et al.. *N. Engl. J. Med.*, 327: 853–857 (1992); Lieherman et al., *J. Clin. Endo. Metab.*, 75: 30–36 (1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993); and U.S. Pat. No. 4,988,675. WO 94/16722 discloses a method of chronic modification of cell barrier properties by exposing a cell to a modification-effective amount of IGF-I for at least about seven days and a method of chronic amelioration or reversal of insulin resistance. However, when IGF-I was used to treat type II diabetes patients in the clinic at a dose of 120–160 µg/kg twice daily, the side effects outweighed the benefit of the treatment. Jabri et al., *Diabetes*, 43: 369–374 (1994). See also Wilton, *Acta Paediatr.*, 383: 137–141 (1992) regarding side effects observed upon treatment of patients with IGF-I.

IGF-I has also been found to exert a variety of actions in the kidney. Hammerman and Miller, *Am. J. Physiol.*, 265:F1–F14 (1993). It has been recognized for decades that the increase in kidney size observed in patients with acromegaly is accompanied by a significant enhancement of glomerular filtration rate. O'Shea and Layish, *J. Am. Soc. Nephrol.*, 3: 157–161 (1992). U.S. Pat. No. 5,273,961 discloses a method for prophylactic treatment of mammals at risk for acute renal failure. Infusion of the peptide in humans with normal renal function increases glomerular filtration rate and renal plasma flow. Guler et al., *Acta Endocrinol.*, 121: 101–106 (1989); Guler et al., *Proc. Natl. Acad. Sci. USA*, 86: 2868–2872 (1989); Hirschberg et al., *Kidney Int.*, 43: 387–397 (1993); U.S. Pat. No. 5,106,832. Further, humans with moderately reduced renal function respond to short-term (four days) IGF-I administration by increasing their rates of glomerular filtration and renal plasma flow. Hence, IGF-I is a potential therapeutic agent in the setting of chronic renal failure. O'Shea et al., *Am. J. Physiol.*, 264: F917–F922 (1993).

Additionally, renal function can be enhanced over a period of days by the administration of IGF-I in the setting of end-stage chronic renal failure. This is important, since end-stage chronic renal failure is a condition that can only be treated with dialysis or transplantation and the incidence thereof is rapidly increasing. Diabetics and the elderly tend to have this condition. Approximately sixty percent of patients with end-stage chronic renal failure are on hemodialysis, about ten percent are on peritoneal dialysis, and the remaining about thirty percent receive a transplant. Dialysis therapy is initiated in over 50,000 patients each year in the United States. An additional 25% of patients who have reached end-stage renal failure are denied access to dialysis each year. The cost of caring for these patients on dialysis currently averages over $200 million a month. Furthermore, the patients exhibit an impaired lifestyle on dialysis. Despite the fact that IGF-I can enhance renal function for those experiencing end-stage chronic renal failure, the enhancements of the glomerular filtration rate and renal plasma flow induced by IGF-I short-term do not persist during long-term administration and incidence of side-effects is high. Miller et al., *Kidney International*, 46: 201–207 (1994).

The dynamics of IGF-I interaction with sensitive tissues are complex and incompletely understood. Biological activity of circulating IGF-I is regulated by levels of plasma IGFBPs, which both enhance and inhibit IGF-I actions. Cohick and Clemmons, *Annu. Rev. Physiol*, 55: 131–153 (1993); Kupfer et al., *J. Clin. Invest.*, 91: 391–396 (1993). In addition, IGFBPs present in tissues regulate the interaction of circulating IGF-I with its receptor. Tissue IGF-I receptor density is altered by changes in levels of circulating IGF-I. In kidney, the numbers of IGF-I receptors are inversely related to levels of circulating IGF-I. Hise et al., *Clin. Sci.*, 83: 223–239 (1991).

It is known that under some circumstances elevated levels of circulating IGF-I are associated with or directly causative of long-term changes in renal function. For example, the enhancements of inulin and PAH clearances that accompany the elevations of circulating GH and IGF-I in patients with acromegaly are sustained over years of time. Ikkos et al., *Acta Endocrinol.*, 21: 226–236 (1956). An increase in creatinine clearance occurred within the first 12 days of IGF-I administration to a GH-insensitive Laron dwarf. The increase was progressive over the next 59 days. Walker et al., *J. Pediatr.*, 121: 641–646 (1992).

GH stimulates the synthesis of IGFBP3 in liver. Hammerman and Miller, supra; Cohick and Clemmons, supra; Kupfer et al., supra. It is the reduction in levels of circulating GH resulting from IGF-I inhibition of pituitary GH release that is thought to result in the fall of circulating IGFBP3 in humans administered IGF-I. Because of their GH insensitivity, IGFBP3 levels are low and are increased by IGF-I in Laron dwarfs. Kenety et al., *Acta Endocrinol.*, 128: 144–149 (1993). This difference or another in the IGF-I effector system could explain the absence of refractoriness to IGF-I in these individuals.

Walker et al., supra, found that IGF-I increased urinary calcium excretion or urinary volume. Miller et al., supra, did not see such effect. IGF-I also enhances the transport of phosphate across the proximal tubular brush border membrane. Quigley and Baum, *J. Clin. Invest.*, 88: 368–374 (1991). Patients with long-standing acromegaly showed marked renal hypertrophy and had supranormal glomerular filtration rates, suggesting that the hyperfiltration that accompanies long-standing elevations of circulating GH and IGF-I in humans is not injurious to the kidney. Ikkos et al., supra; Hoogenberg et al., *Acta Endocrinol.*, 129: 151–157 (1993).

For complete reviews of the effect of IGF-I on the kidney, see, e.g., Hammerman and Miller, *Am. J. Physiol.*, 265: F1–F14 (1993) and Hammerman and Miller, *J. Am. Soc. Nephrol.*, 5: 1–11 (1994).

As to anabolic indications for IGF-I, in HIV-infected patients treated consecutively with IGF-I, the IGF-I promoted anabolism but tachyphylaxis developed rapidly in the patients. Lieherman et al., *U.S. Endocrine Meeting*, June 1993 (Abst. 1664), disclosed more fully by Lieherman et al., *J. Clin. Endo. Metab.*, 78: 404–410 (1994). In patients with severe head injuries, a condition associated with profound hypercatabolism and nitrogen loss, infusion of IGF-I produced only a transient positive nitrogen balance. In the first week the patients experienced a positive nitrogen balance, but during the second week, a negative nitrogen balance developed. Chen et al., *U.S. Endocrine Meeting*, June 1993 (Abst. 1596).

All of these studies indicate that there is a need in the art for a treatment with IGF-I that does not subside after a certain period of treatment time and one that both maximizes efficacy and minimizes the side effects of IGF-I.

SUMMARY OF THE INVENTION

Accordingly, this invention supplies a method for administering IGF-I to a mammal in an intermittent fashion so as to sustain its biological response in the treatment of a chronic disorder in the mammal comprising administering a therapeutically effective amount of IGF-I to the mammal to provide an exposure to IGF-I for a period of time that provides the maximum biological response in the mammal, then discontinuing said administration for a period of time equal to or less than the time period during which the IGF-I was previously administered, then administering a therapeutically effective amount of IGF-I to the mammal to provide an exposure to IGF-I for a period of time that provides the maximum biological response in the mammal, then discontinuing said administration for a period of time equal to or less than the time period during which the IGF-I was just previously administered, and repeating this pattern of administration and discontinuance of administration for as long as necessary to achieve or maintain sustained biological response in the mammal.

In a preferred embodiment, the chronic disorder is chronic renal failure, diabetes, a cardiac disorder such as congestive heart failure, an anabolic disorder, an immunological disorder, a neurological disorder, or a combination of such disorders.

In another aspect, this invention supplies a method for treating chronic renal failure in a mammal by treating with IGF-I in an intermittent fashion comprising administering a therapeutically effective amount of IGF-I to the mammal to provide an exposure to IGF-I for from about three to twelve days, then discontinuing said administration for from about two to seven days, then administering a therapeutically effective amount of IGF-I to the mammal to provide an exposure to IGF-I for from about three to twelve days, then discontinuing said administration for from about two to seven days, and repeating this pattern of administration and discontinuance of administration for as long as necessary to achieve or maintain sustained renal function in the mammal, said time periods of discontinuing administration being for a period of time equal to or less than the time period during which the IGF-I was just previously administered.

DETAILED DESCRIPTION OF THE PREFERRED EMBODIMENTS

Definitions

Figure 1:
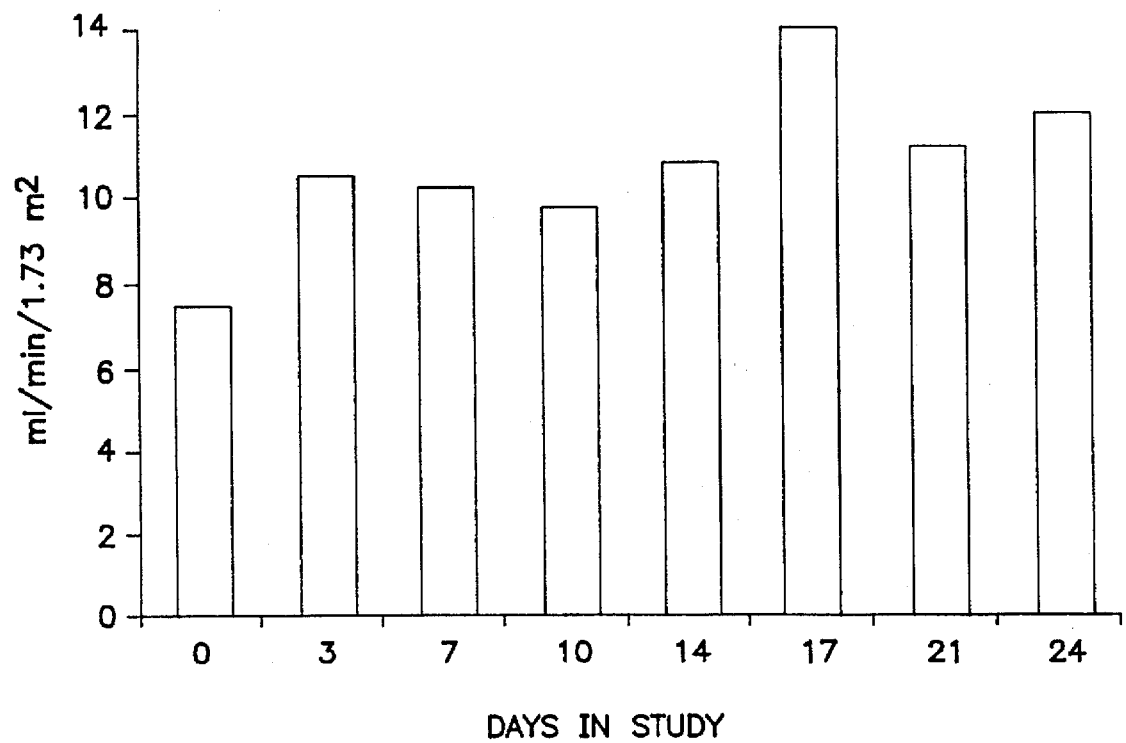
FIG. 1 depicts inulin clearance for five patients as a function of days in the study.

As used herein, "biological response" refers to the favorable response of a mammal having a specific chronic disorder to treatment with IGF-I. Maximizing the response means improving efficacy but at the same time avoiding or at least minimizing the occurrence of side effects. The response is tailored to the disorder being treated. Thus, for example, "biological response" in the context of end-stage chronic renal failure, or "improved kidney function" refers to delaying the time a patient has to go on dialysis by at least one month. "Biological response" in the context of diabetic indications refers to decreasing a mammal's blood sugar levels, and reducing markers of glycemic control such as hemoglobin $A1_c$. In the context of anabolic disorders, the phrase refers to increasing anabolic parameters and clinical phenotypes. In the context of cardiac disorders, the phrase refers to improvement in cardiac function. "Sustained biological response" refers to maintaining the biological response (without substantial side effects) for an extended period of time as is considered appropriate for the disorder in question.

A "period that provides the maximum biological response" refers to a time period representing the maximum time required to obtain and maintain, or to stimulate, the favorable biological response in the mammal. This amount of time will depend, for example, on the type of mammal being treated, the type of disorder being treated, and the dose being administered (to avoid side-effects). Preferably, this amount will be in the range of from about three to twelve days, more preferably three to five days or seven to twelve days, when the treatment cycle is a total of seven days or 14 days, respectively.

"Provide an exposure to IGF-I" refers to an exposure that is continuous or in consecutive days (at least once a day consecutively) over the period of days specified. This may be accomplished, for example, by daily or twice daily injections, or by long-acting formulations of IGF-I that are taken once but provide continuous exposure of the mammal to the IGF-I for the duration of the desired exposure period of the treatment. The discontinuance of treatment for injections of at least daily frequency is a continual or daily consecutive lack of treatment for the period specified. The discontinuance of treatment for long-acting formulations begins when the blood levels of IGF-I have fallen below the desired or maximum level for efficacious treatment and ends when the IGF-I is again administered to the mammal.

Treatment refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion refers to treatment that is not consecutive, but rather cyclic in nature. The treatment regime herein involves short-term administration on an intermittent basis as part of a single, long-term course of treatment.

One method of judging the correct intermittent regimen for a particular indication of use is to administer IGF-I by daily injection until the time of the maximal effect of the drug is obtained and before the biological response wanes or until side effects occur to any significant degree, whichever occurs earlier. This is the most suitable period of treatment as defined herein. The maximum period of rest from treatment will be an equivalent, or more usually a lesser, interval of time. Hence, the two gauges of the intermittent regime that is most appropriate are the maximum efficacy observed and the occurrence of side effects, with the treatment being tailored to minimize the side effects seen in a particular disease state.

"Side effects" refer to effects of treatment with IGF-I that are not the intended effects such as, e.g., cardiac effects including syncopal episodes with lightheadedness, fainting and seizure activity, bradycardia associated with nausea and dizziness, transient atrial fibrillation, hypoglycemia, and asymptomatic tachycardia. Other side effects include Bell's palsy, intracranial hypertension, papilledema, hypokalemia, mild weight gain, dyspnea, bilateral jaw tenderness, orthostatic hypotension, local burning or pain at the injection site, headaches including migraine headaches, abdominal pain, sinusitis, jaw pain, edema, paratid swelling, myalgias, arthralgias, fatigue, weakness, snoring, breast enlargement, back pain, flushing, difficulty breathing, transient hypertension, kidney stones, and coarsing of facial features. Effects on breathing include tonsillar and adenoidal enlargement and acute pulmonary edema, and adverse effects on blood cells include thrombocytopemic purpura and neutropenia.

As used herein "chronic" refers to a disorder that is not acute but rather occurs more or less on a continuous level. A "disorder" is any condition that would benefit from treatment with IGF-I, including but not limited to, for example, chronic lung disease, hyperglycemic disorders as set forth below, chronic renal disorders, such as chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as increasing lean mass-to-fat ratios, immunological disorders such as immunodeficiencies including decreased CD4 counts and decreased immune tolerance or chemotherapy-induced tissue damage, bone marrow transplantation, diseases or insufficiencies of cardiac structure or function such as chronic heart conditions and congestive heart failure, chronic neuronal, neurological, or neuromuscular disorders, e.g., peripheral neuropathy, multiple sclerosis, myotonic dystrophy, catabolic states associated with wasting caused by any condition, including, e.g., trauma or wounding or infection such as with a bacterium or human virus such as HIV, Laron dwarfism, wounds, skin disorders, gut structure and function that need restoration, and so forth. The disorder being treated may be a combination of two or more of the above disorders.

For purposes herein, "hyperglycemic disorders" refers to all forms of diabetes, such as type I and type II diabetes, as well as hyperinsulinemia and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially type II diabetes.

"Long-acting formulations" of IGF-I refer to formulations that maintain levels of exogenously administered IGF-I in the blood for an extended period of time, generally beyond one day, so that injections need not be given on a daily basis. Long-acting formulations include, for example, sustained-release formulations, IGF-I that is PEGylated, and IGF-I formulated or complexed with an IGF binding protein.

Mammal for purposes of treatment refers to any animal classified as a mammal, including humans, domestic and farm animals, and zoo, sports, or pet animals, such as dogs, horses, cats, sheep, pigs, cows, etc. Preferably, the mammal herein is human.

As used herein, IGF-I refers to insulin-like growth factor-I from any species, including bovine, ovine, porcine, equine, avian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276; WO 87/01038; and WO 89/05822, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

Modes for Carrying out the Invention

The IGF-I is administered to the mammal by any suitable technique, depending mainly on the nature of the disorder and type of mammal, including parenterally, intranasally, intrapulmonary, orally, or by absorption through the skin. It can be administered locally or systemically. Examples of parenteral administration include subcutaneous, intramuscular, intravenous, intraarterial, and intraperitoneal administration. This includes injections (single or multiple, e.g., 1-4 per day) or infusions. Preferably, the IGF-I is administered by daily or twice daily subcutaneous injections or by subcutaneous or intravenous infusion.

The IGF-I to be used in the therapy will be formulated and dosed in a fashion consistent with good medical practice, taking into account the clinical condition of the individual patient (especially the side effects of treatment with IGF-I as noted above), the site of delivery of the IGF-I composition, the method of administration, the scheduling of administration, and other factors known to practitioners. The incidence of side effects of IGF-I may be reduced by decreasing the dose. Kupfer et al., supra; Hartman et al., *J. Clin. Invest.*, 91: 2453-2462 (1993). The effective amount of IGF-I for purposes herein is thus determined by such considerations and is an amount that increases and maintains the relevant, favorable biological response of the mammal.

As a general proposition, the total pharmaceutically effective amount of IGF-I administered parenterally per dose will be in the range of about 5 to 1000 µg/kg/day, preferably 10 to 500 µg/kg/day, more preferably about 30 to 200 µg/kg/day, of patient body weight, although, as noted above, this will be subject to a great deal of therapeutic discretion. For example, with treatment of chronic renal failure, the dose per day is preferably about 10 to 160 µg/kg, more preferably 20 to 100 µg/kg, and most preferably about 25 to 75 µg/kg.

The period of treatment with IGF-I is that which provides a maximum biological response as defined above, preferably about 3 to 12 days, more preferably 3-8 days, most preferably 4-7 days, and the off-treatment period is about 2-10 days, more preferably 2-8 days, most preferably 2-7 days. In a particularly preferred embodiment, the on-treatment period is about 3-5 days for a 7-day cycle and about 7-12 days for a 14-day cycle, and the off-treatment period is about 2-4 days for a 7-day cycle and about 2-7 days for a 14-day cycle. The specific length of these periods depends mainly on efficacy data, side effects if any, the time required to achieve maximum biological response, the maximum time required for maintenance of a biological response; and, for the off-treatment, the period of treatment employed as noted below. The treatment pattern of administering IGF-I and then stopping administration thereof is repeated until the desired maintained biological response is obtained in the mammal. In one embodiment, the same length of treatment and discontinuance of treatment is repeated and the same dosing is used during each cycle; however, the invention also encompasses the situation where each cycle of on and off treatment involves a different period of time and/or dosing. For example, if side effects were observed during the initial treatment period, the repeated treatment period and/or dosing might be reduced, whereas if efficacy increases during the first treatment with no substantial side effects, the second period of treatment and/or dosing might be increased.

The on- and off-treatment periods of time are proportionate and interdependent, such that the period of time when treatment is not carried out is no longer than the period when treatment is carried out. For example, if the patient is treated for 4 days with IGF-I, he or she can be off treatment for up to 3 days, but not for 4 or more days; at that point the patient needs to be treated again with IGF-I. In a preferred embodiment, the cycle of treatment adds up to a total of 7 days or 14 days to ease tracking of the treatment by the patients. The table below illustrates this scheme:

| On treatment | Off treatment |
| --- | --- |
| 4 days | 3 days |
| 5 days | 2 days |
| 6 days | 1 day |
| 7 days | 7 days |
| 8 days | 6 days |
| 9 days | 5 days |
| 10 days | 4 days |
| 11 days | 3 days |
| 12 days | 2 days |

One of the purposes of the intermittent therapy with IGF-I is to maintain stable plasma levels of some of the IGF binding proteins to facilitate the most appropriate treatment with IGF-I. Alternatively, the IGF-I may be formulated so as to have a continual presence in the blood during the course of treatment, as for example by being made into a long-acting formulation, e.g., by being covalently attached to a polymer such as polyethylene glycol (PEG). In this embodiment, fewer injections could be given in each course of treatment due to the persistence of the IGF-I in the body by way of the long-acting nature of the preparation. In this embodiment, if each injection causes an exposure of several days, the single injections tailored to give exposures as described above would be the regimen used. If the formulation is long-acting, the injections are suitably given at weekly intervals or at multiples of weekly intervals.

Suitable examples of sustained-release preparations, which are one type of long-acting formulation, include semi-permeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167-277 [1981] and Langer, *Chem. Tech.*, 12: 98-105 [1982] or poly (vinylalcohol)), polylactides (U.S. Pat. No. 3,773,919, EP 58,481), copolymers of L-glutamic acid and gamma ethyl-L-glutamate (Sidman et al., *Biopolymers*, 22: 547-556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), polylactate polyglycolate (PLGA), and poly-D-(–)-3-hydroxybutyric acid (EP 133,988). The IGF-I also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release IGF-I compositions also include liposomally entrapped IGF-I. Liposomes containing IGF-I are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the most suitably IGF-I therapy. A specific example of a suitable sustained-release formulation is in EP 647,449.

For parenteral administration, in one embodiment, the IGF-I is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer s solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

The IGF-I is typically formulated in such vehicles at a concentration of about 0.1 mg/mL to 100 mg/mL, preferably 1–10 mg/mL, at a pH of about 4.5 to 8. Full-length IGF-I is preferably formulated at a pH about 5–6, and des(1–3)-IGF-I is preferably formulated at a pH about 3.2 to 5. It will be understood that use of certain of the foregoing excipients, carriers, or stabilizers will result in the formation of IGF-I salts.

While the IGF-I can be formulated in any way suitable for administration, the preferred formulation contains about 2–20 mg/mL of IGF-I, about 2–50 mg/mL of an osmolyte, about 1–15 mg/mL of a stabilizer, and a buffered solution at about pH 5–6, more preferably pH about 5–5.5. Preferably, the osmolyte is an inorganic salt at a concentration of about 2–10 mg/mL or a sugar alcohol at a concentration of about 40–50 mg/mL, the stabilizer is benzyl alcohol or phenol, or both, and the buffered solution is an acetic acid salt buffered solution. More preferably, the osmolyte is sodium chloride and the acetic acid salt is sodium acetate. Even more preferably, the amount of IGF-I is about 8–12 mg/mL, the amount of sodium chloride is about 5–6 mg/mL, the amount of benzyl alcohol is about 8–10 mg/mL, the amount of phenol is about 2–3 mg/mL, and the amount of sodium acetate is about 50 mM so that the pH is about 5.4. Additionally, the formulation can contain about 1–5 mg/mL of a surfactant, preferably polysorbate or poloxamer, in an amount of about 1–3 mg/mL. Alternatively, the formulation is suitably IGF-I dissolved at 5 mg/ml in 10 mM citrate buffer and 126 mM NaCl at pH 6.

IGF-I to be used for therapeutic administration is preferably sterile. Sterility is readily accomplished by filtration through sterile filtration membranes (e.g., 0.2 micron membranes). Therapeutic IGF-I composition generally is placed into a container having a sterile access port, for example, an intravenous solution bag or vial having a stopper pierceable by a hypodermic injection needle.

The IGF-I ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-I solutions, and the resulting mixture is lyophilized. The infusion solution is prepared by reconstituting the lyophilized IGF-I using bacteriostatic Water-for-Injection.

IGF-I can be administered along with a low-protein diet or with a low-protein diet in conjunction with nutrient supplements such as ketoacid supplements.

In addition, the IGF-I is appropriately administered together with any one or more of its binding proteins, for example, those currently known, i.e., IGFBP1, IGFBP2, IGFBP3, IGFBP4, IGFBP5, or IGFBP6, or with the acid-labile subunit (ALS) of the IGF binding complex. Such proteins may be administered separately or as a complex with the IGF-I. The IGF-I may also be coupled to a receptor or antibody or antibody fragment for administration. The preferred binding protein for IGF-I herein is IGFBP3, which is described in U.S. Pat. No. 5,258,287 and by Martin and Baxter, *J. Biol. Chem.*, 261: 8754–8760 (1986). This glycosylated IGFBP3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151. Briefly, the IGF-I and IGFBP are administered in effective amounts by subcutaneous bolus injection in a molar ratio of from about 0.5:1 to about 3:1, preferably about 1:1.

In a further embodiment, depending on the chronic disorder being treated, another drug besides IGF-I or IGFBP is administered in conjunction with the IGF-I. For example, for a renal indication, it may be desirable to administer in conjunction with IGF-I other renally active molecules that promote reabsorption and retention of electrolytes such as, e.g., atrial natriuretic peptide (ANP), ANP analogs, or any variants thereof with or without receptor activity, urodilatin, human B-type natriuretic peptide (BNP), angiotension receptor antagonist, vasopressin and its analogs, and endothelin antagonists such as antibodies or peptide antagonists. One example is BQ-123 (Ihara et al., *Life Science*, 50: 247–250 [1992]; JP 51-94254A published Aug. 3, 1993; Webb et al., *Biochem. Biophys. Res. Comm.*, 185: 887–892 [1992]), a cyclic pentapeptide that is a potent and specific blocker of endothelin A receptors and blocks only the hypertrophic activity induced by endothelin-1, not CT-1, mouse LIF, or phenylephrine. Another example is the parent compound to BQ-123 described by Ihara et al., *Biochim. Biophys. Res. Comm.*, 178: 132–137 (1991). Further examples include those described in EP 647,236; EP 647,449; EP 633,259 (phenyl-sulfonyl amino-pyrimidine derivatives); EP 601,386 (sulfonamide compounds); U.S. Pat. No. 5,292,740 (phenylsulfonamidopyrimidines); and U.S. Pat. No. 5,270,313 (phenyl-sulfonyl-aminopyrimidine derivatives). In addition, angiotensin-converting enzyme (ACE) inhibitors may be beneficial in conjunction with the IGF-I treatment of renal disorders.

In the treatment of congestive heart failure, ACE inhibitors may be useful together with IGF-I by reducing systemic vascular resistance and relieving circulatory congestion. The ACE inhibitors include but are not limited to those designated by the trademarks Accupril® (quinapril), Altace® (ramipril), Capoten® (captopril), Lorensin® (benazepril), Monopril® (fosinopril), Prinivil® (lisinopril), Vasotec® (enalapril), and Zestril® (lisinopril). One example of an ACE inhibitor is that sold under the trademark Capoten®. Generically referred to as captopril, this ACE inhibitor is designated chemically as 1-[(2S)-3-mercapto-2-methylpropionyl]-L-proline.

As another example of combination therapy, for an anabolic indication, it may be desirable to administer both IGF-I and GH to the mammal, each in effective amounts, or each in amounts that are sub-optimal but when combined are effective. Preferably, such amounts are about 50 to 100 μg/kg/day of IGF-I and about 0.3 mg/kg/week GH. Preferably, if GH and IGF-I are administered together, the administration of both IGF-I and GH is by injection using, e.g., intravenous or subcutaneous means. More preferably, the administration is by subcutaneous injection for both IGF-I and GH, most preferably daily injections.

It is noted that practitioners devising doses of both IGF-I and GH should take into account the known side effects of treatment with these hormones. For GH, the side effects include sodium retention and expansion of extracellular volume (Ikkos et al., *Acta Endocrinol.* (Copenhagen), 32: 341–361 [1959]; Biglieri et al., *J. Clin. Endo. Metab*, 21: 361–370 [1961]), as well as hyperinsulinemia and hyperglycemia. The side effects of IGF-I are noted above. Indeed, the combination of IGF-I and GH may lead to a reduction in the unwanted side effects of both agents (e.g., hypoglycemia for IGF-I and hyperinsulinism for GH) and to a restoration of blood levels of GH, the secretion of which is suppressed by IGF-I.

The IGF-I and GH, preferably the full-length IGF-I, may be administered separately or may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

The preferred combined composition comprises IGF-I and GH in a weight ratio of IGF-I:GH of between about 1:1 and 100:1 (w/w), about 0.05–0.3 mM of an osmolyte, about 0.1–10 mg/mL of a stabilizer, about 1–5 mg/mL of a surfactant, and about 5–100 mM of a buffer at about pH 5–6. Preferably, the osmolyte is an inorganic salt and the surfactant is nonionic. More preferably, the inorganic salt is sodium chloride or potassium chloride, the stabilizer is phenol or benzyl alcohol, the surfactant is polysorbate or poloxamer, the buffer is sodium acetate or sodium citrate or both, and the amounts of IGF-I and GH are about 2–20 mg/mL and about 0.2–10 mg/mL, respectively, with the weight ratio of IGF-I:GH being between about 1:1 and 50:1. Even more preferably, the amount of IGF-I is about 5–10 mg/mL, the amount of GH is about 1–5 mg/mL, the weight ratio of IGF-I:GH is about 1:1 to 4:1, the amount of sodium chloride is about 5–7 mg/mL, the amount of phenol is about 0.1–3 mg/mL, the amount of benzyl alcohol is about 6–10 mg/mL, the surfactant is polysorbate in an amount of about 1–3 mg/mL, the amount of sodium acetate is about 2.5–4 mg/mL, and the amount of sodium citrate is about 0.1–1 mg/mL.

The following examples are offered by way of illustration and not by way of limitation. The disclosures of all citations in the specification are expressly incorporated herein by reference.

EXAMPLE I

Introduction

Renal function can be enhanced by administration of IGF-I at 100 μg/kg subcutaneously each day in the morning for four days in the setting of end-stage chronic renal failure as established by Miller et al., supra. However, renal function returned to the baseline level at 28 days despite ongoing, continuous treatment with IGF-I. In contrast, Example I shown herein demonstrates ongoing efficacy when intermittent dosing is given in the context of end-stage chronic renal failure.

Methods

Five individuals over eighteen years of age with end-stage chronic renal insufficiency (ESRD), defined as a creatinine clearance less than 15 mL/min/1.73 $m^2$ within the last six months and having characteristic symptoms of ESRD, were selected for the study. Patients with a single kidney or a history of malignancy were excluded from the study.

Patient 1 was a 71-year-old Caucasian female with ESRD secondary to Type II diabetes mellitus. Her diabetes was of 10 years duration and was complicated by retinopathy, neuropathy, and nephropathy. Symptoms on admission included mild intermittent nausea, pruritus, and decreased exercise tolerance.

Patient 2 is a 64-year-old Caucasian female with ESRD secondary to chronic glomerulosclerosis and hypertension. The patient was noted to have renal impairment approximately 5 years ago. She was treated with prednisone but could not tolerate the therapy as she developed steroid-induced psychosis. She had experienced progressive deterioration of renal function. Symptoms on admission included nausea, pruritus, edema, and decreased exercise tolerance.

Patient 3 is a 52-year-old Caucasian male with a history of ESRD secondary to chronic glomerulonephritis and hypertension. The patient was first noted to have mild impairment of renal function 20 years ago. He was treated with steroids without any response. Over the last several years he has had progressive deterioration of his renal function. Symptoms at the time of admission were severe nausea, pruritus, shortness of breath, and decreased exercise tolerance.

Patient 4 is a 59-year-old Caucasian female with a history of ESRD secondary to interstitial nephritis. The patient was diagnosed with Crohn's disease, requiring a partial colectomy at age 39. Unfortunately, she was left with inadequate bowel and has suffered with chronic malabsorption. Three years ago she was noted to have an elevated creatinine level. A renal biopsy demonstrated interstitial nephritis and she has experienced progressive deterioration of renal function. Symptoms at the time of admission were pruritus, sleep disturbance, and decreased exercise tolerance.

Patient 5 is a 49-year-old Caucasian male with a history of ESRD secondary to autosomal dominant polycystic kidney disease. The patient was diagnosed 20 years ago when his father developed renal failure. Over the last 10 years he has experienced progressive decline in renal function. Symptoms at the time of admission were pruritus, intermittent nausea, and decreased exercise tolerance.

The study protocol was approved by the Human Studies Committee of Washington University. Informed consent was obtained and patients were admitted to the Washington University General Clinical Research Center (GCRC) and placed on a diet of 35 kcal/kg/day, 2 g sodium/day, and 0.8 g/kg protein/day. Subjects remained on the standardized diet throughout the duration of the study.

Patients participated in protocols of 4 to 20 weeks in duration. The first day of the protocols was designated as day 0. On day 0, measurements of blood urea nitrogen (BUN), serum $Na^+$, $K^+$, $HCO_3^-$, IGF-I, IGFBP1, -2, and -3, creatinine, calcium, and phosphate were obtained in addition to inulin and PAH clearances. BUN, serum $Na^+$, $K^+$, $HCO_3^-$, creatinine, calciums phosphate, and glucose levels were measured on an Hitachi 747™ autoanalyzer (Boehringer Mannheim, Indianapolis, Ind.). IGF-I and IGFBP levels in serum were measured by Endocrine Sciences (Calabasas Hills, Calif.). Dunnett's multiple comparison procedure (Miller et al., supra) was used for multiple comparisons. Values were considered significantly different if $p<0.05$ for 2-tailed analysis. The data were analyzed using one-way analysis of variance (ANOVA) (Instat, Graph Pad Software Inc., San Diego, Calif.).

On days 1 through 4 the patients received rhIGF-I dissolved at 5 mg/ml in 10 mM citrate buffer and 126 mM NaCl at pH 6 (provided by Genentech, Inc., South San Francisco, Calif.) at a dose of 50 µg/kg subcutaneously once per day at 8 AM (QAM). These patients were not treated with IGF-I on days 5 through 7 and then treated again on days 8 through 11 and then not treated on days 12 through 14 and then treated, using this administration/dosing pattern for a period of 4 to 20 weeks. Blood samples were obtained on the first and fourth day, at the beginning and end of each cycle of treatment, of each week for the first four weeks, to determine inulin and PAH clearances and IGF-I, IGFBP1, IGFBP2, and IGFBP3 levels.

Results

Figure 2:
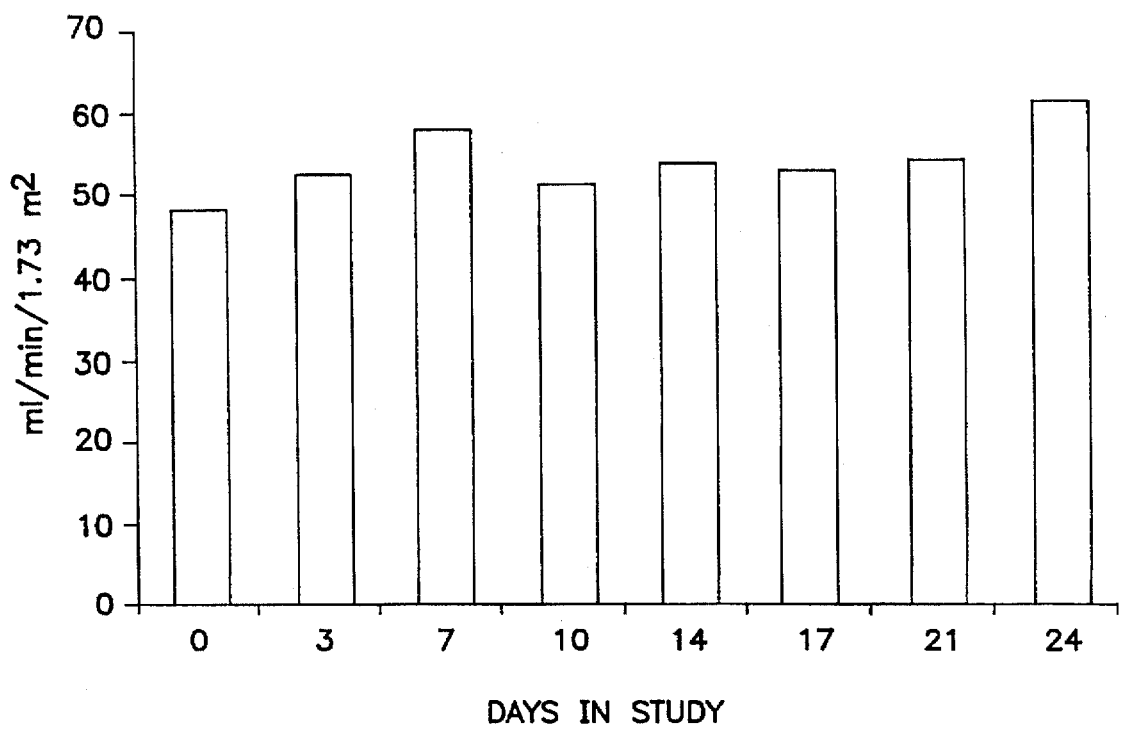
FIG. 2 depicts PAH clearance for five patients as a function of days in the study.
Figure 3:
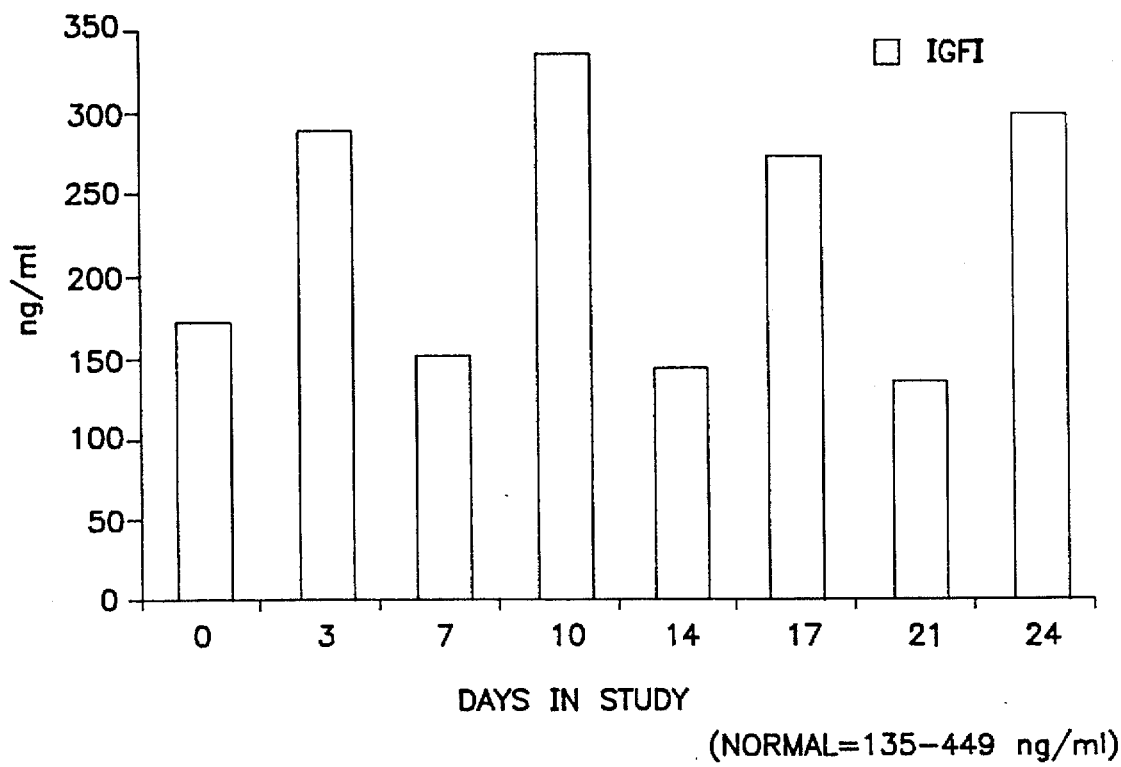
FIG. 3 depicts IGF-I levels for five patients as a function of days in the study (normal is 135–449 ng/mL).
Figure 4:
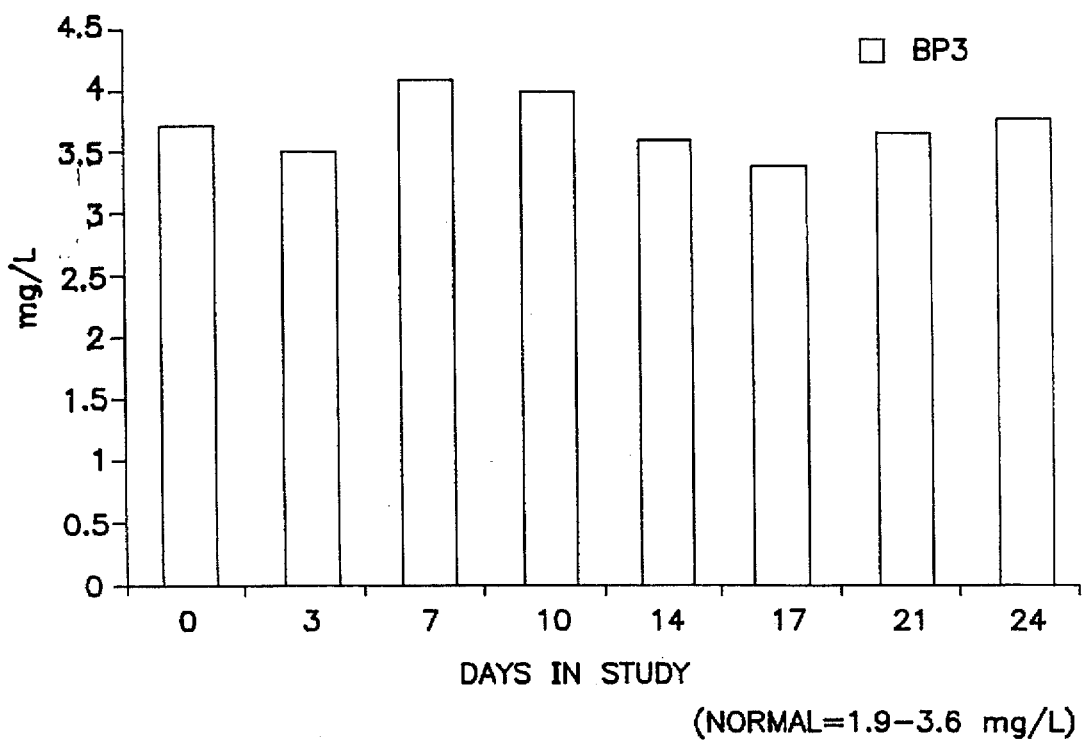
FIG. 4 depicts IGFBP3 levels for five patients as a function of days in the study (normal is 1.9–3.6 mg/L).
Figure 5:
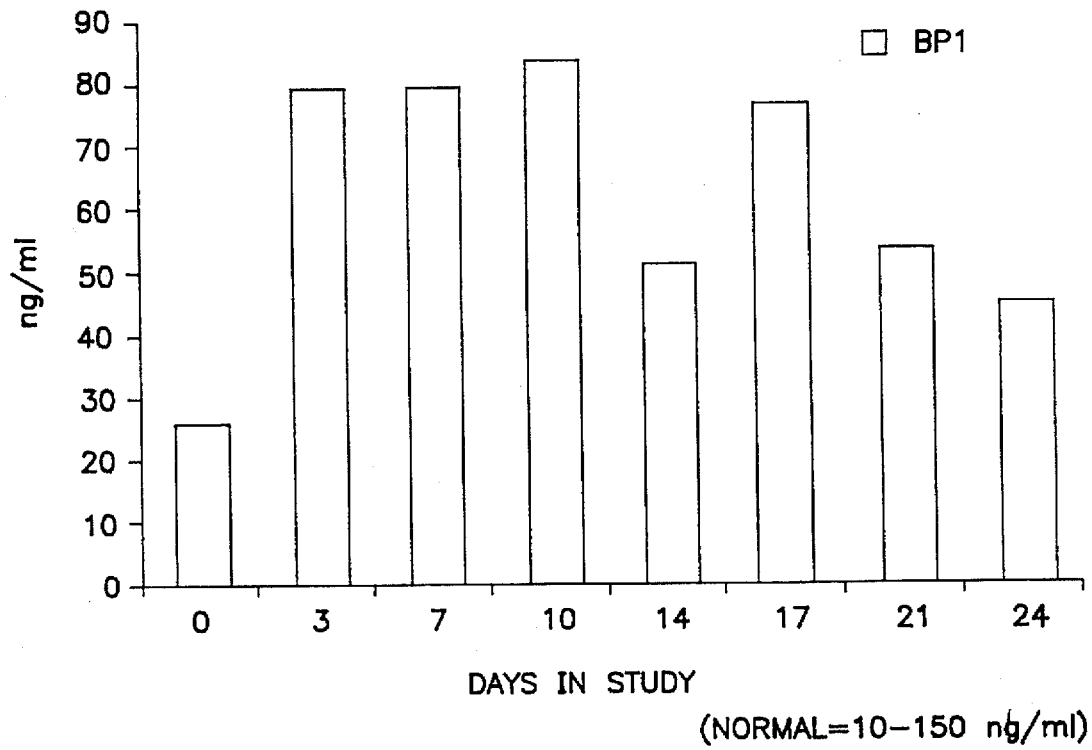
FIG. 5 depicts IGFBP1 levels for five patients as a function of days in the study (normal is 10–150 ng/mL).
Figure 6:
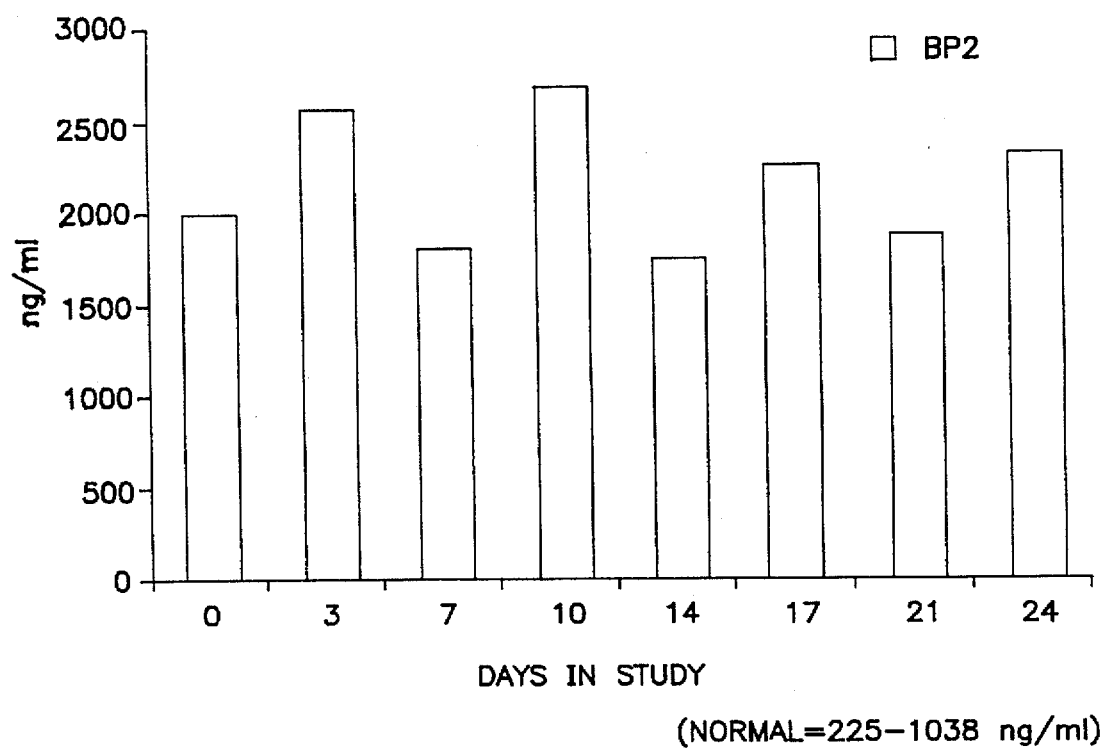
FIG. 6 depicts IGFBP2 levels for five patients as a function of days in the study (normal is 225–1038 ng/mL).
Figure 7:
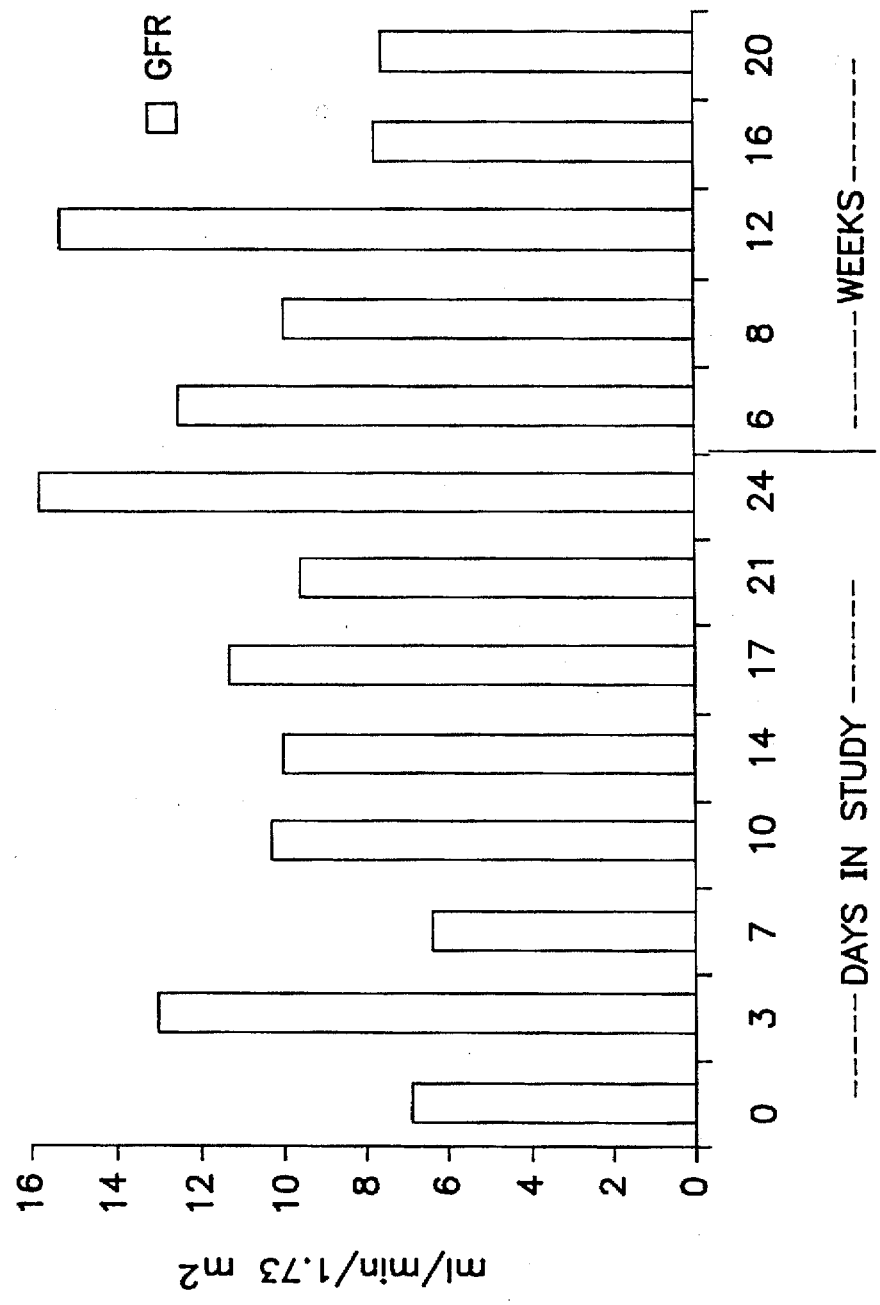
FIG. 7 depicts inulin clearance in Patient 2 as a function of days in the study and weeks in the study.
Figure 8:
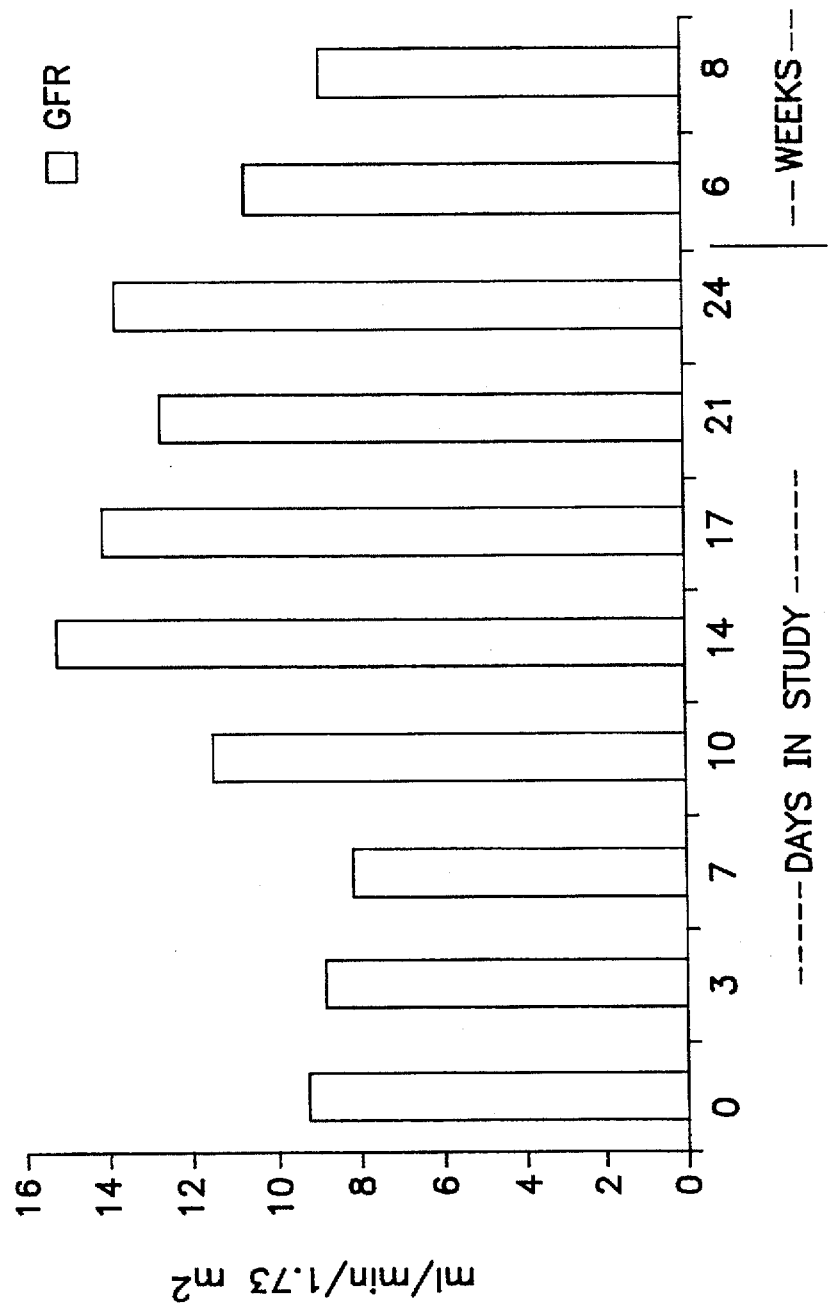
FIG. 8 depicts inulin clearance in Patient 3 as a function of days in the study and weeks in the study.
Figure 9:
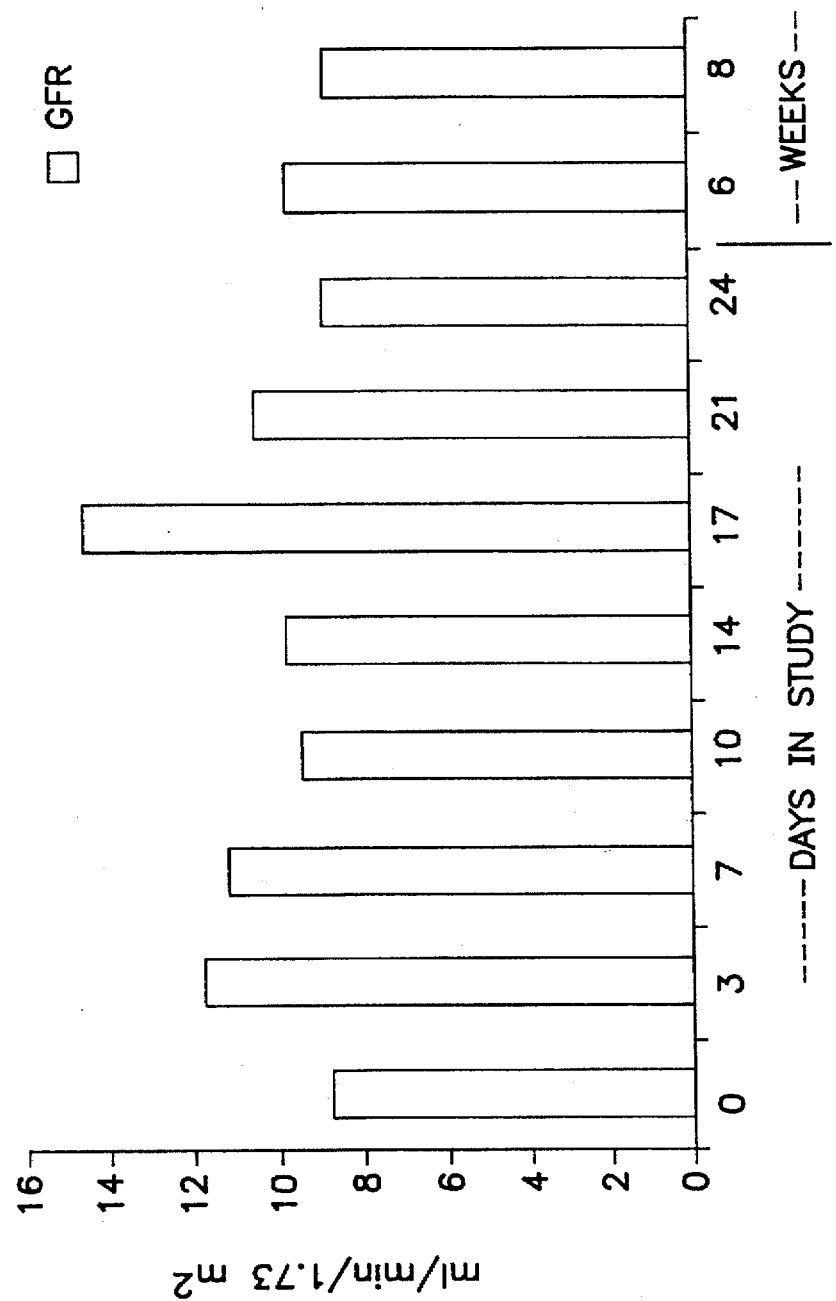
FIG. 9 depicts inulin clearance in Patient 4 as a function of days in the study and weeks in the study.
Figure 10:
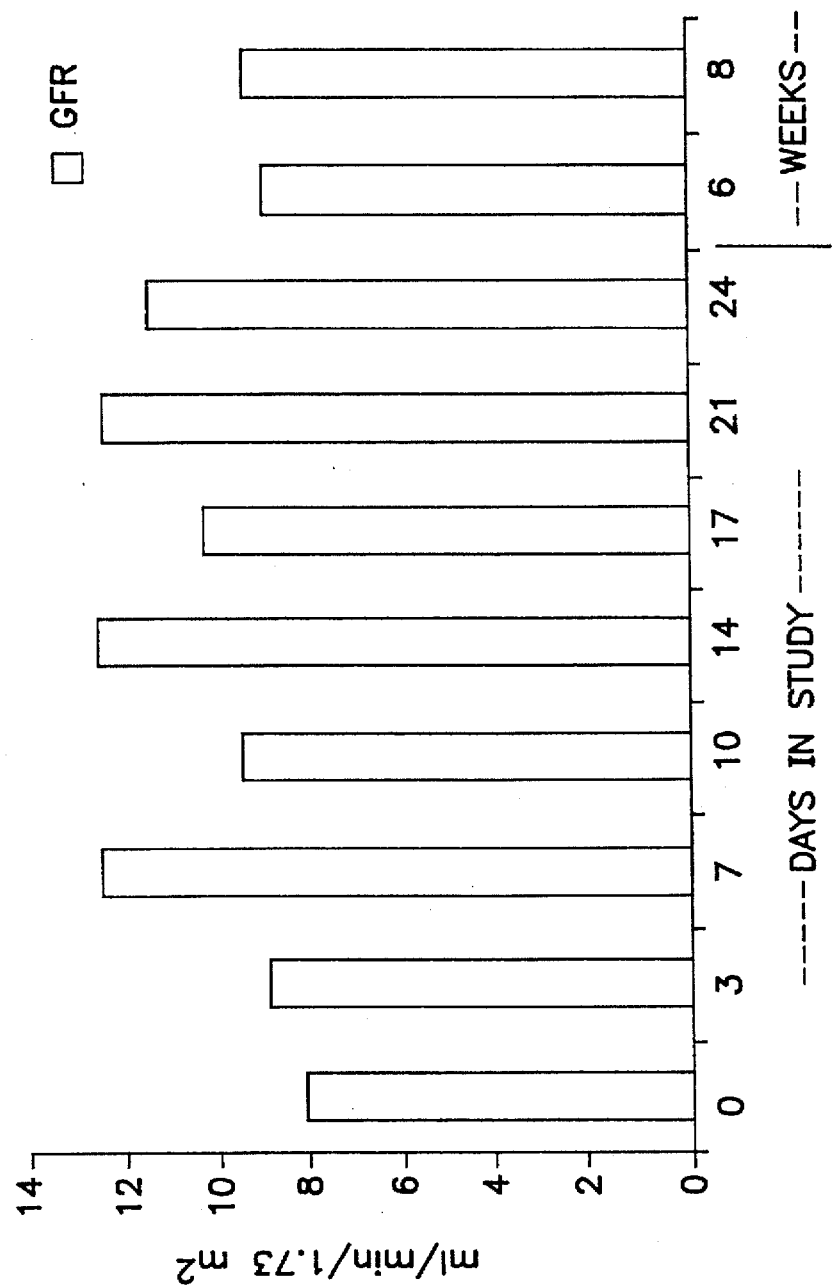
FIG. 10 depicts inulin clearance in Patient 5 as a function of days in the study and weeks in the study.
Figure 11:
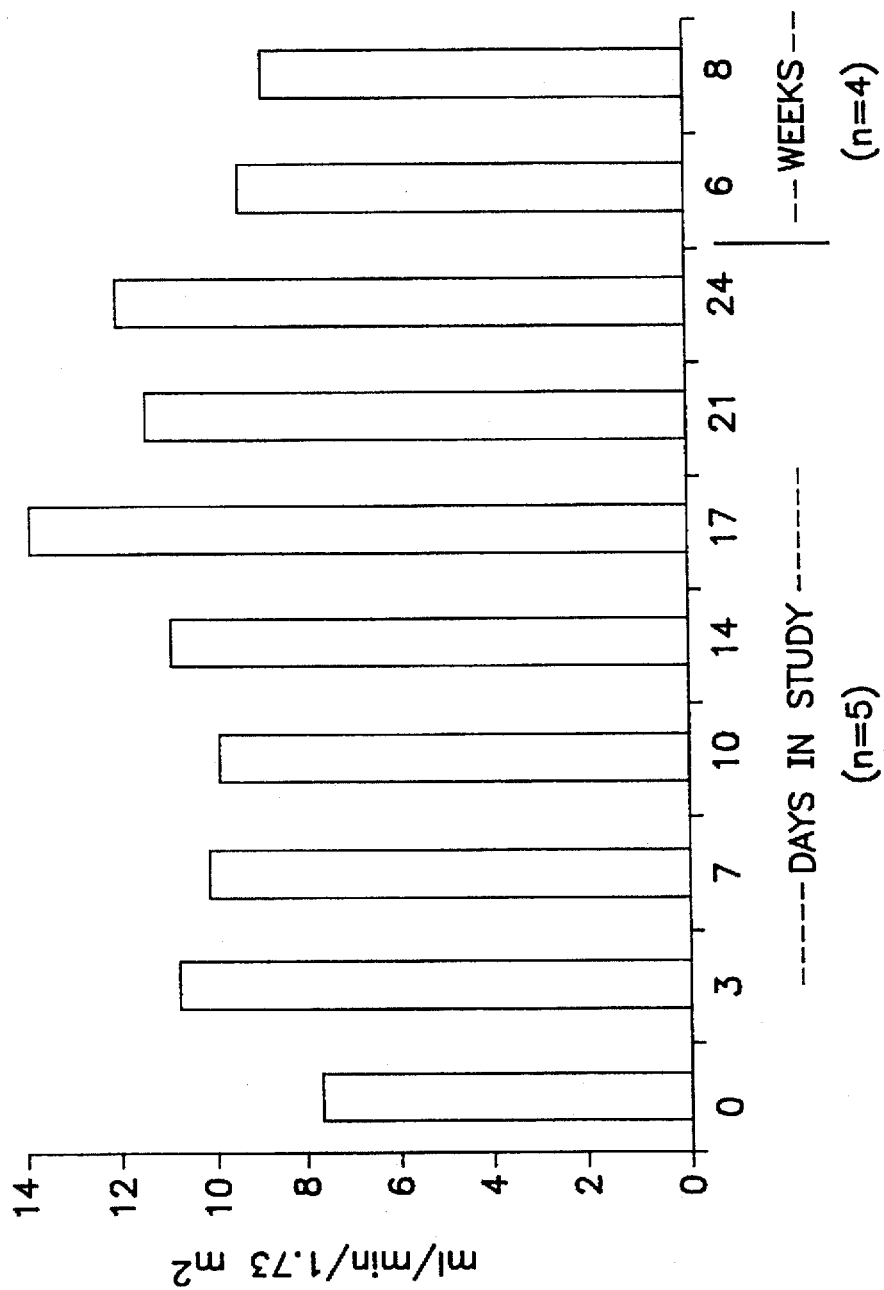
FIG. 11 depicts inulin clearance for five patients as a function of days in the study and weeks in the study.

FIG. 1 shows the inulin clearance for patients 1–5 for up to 24 days in the study. It can be seen that the inulin clearance progressively increased during the course of the treatment regimen of intermittent IGF-I. FIG. 2 shows the PAH clearance for patients 1–5 for up to 24 days in the study. It can be seen that PAH clearance also increased with the treatment regimen. FIG. 3 shows the IGF-I levels for patients 1–5 for up to 24 days in the study. It can be seen that IGF-I levels rise and fall with the intermittent treatment regimen but that IGF-I levels are maintained with each cycle of treatment. FIG. 4 shows the IGFBP3 levels for patients 1–5 for up to 24 days in the study. It can be seen that these levels generally are stable throughout the 24 days of the study. FIG. 5 shows the IGFBP1 levels for patients 1–5 for up to 24 days in the study. It can be seen that these levels generally rise with the treatment regimen. FIG. 6 shows the IGFBP2 levels for patients 1–5 for up to 24 days in the study. These levels rise and fall with the intermittent treatment regimen. FIGS. 7–10 respectively show the inulin clearance patterns for patients for a period of days and weeks in the study. FIG. 11 demonstrates the mean inulin clearance of the five patients treated for 24 days and the four patients that continue on IGF-I for up to 8 weeks.

The intermittent dosage treatment delayed by ten weeks the time that Patient 3, who was in the worst condition at baseline of the five patients studied, had to undergo dialysis. The other four patients did not need to be subjected to dialysis. The exercise tolerance for all five patients was improved. The side effects experienced were minimized, with local irritation at the site of injection in two of the five patients studied being a minor effect. The glomerular filtration rate (GFR) for the five patients increased to 12.0 mL/min/1.73 $m^2$ on day 24 of the study, an increase of 56% over baseline. Most patients require dialysis when the clearance rate is below 10.0 mL/min/1.73 $m^2$. When compared to baseline, there was a statistically significant elevation in the combined inulin clearances for patients 1–5 when examined at days 14, 17, 21, and 24.

The symptoms and routine laboratory studies of the five patients (baseline and treatment) are provided in Tables I and II, respectively. The means and standard errors on FIGS. 1–6 are provided in Table III.

TABLE I

Symptoms

| Symptoms | Admission | 1 Month |
|---|---|---|
| Nausea | 4/5 | 0/5 |
| Pruritus | 5/5 | 0/5 |
| Edema | 1/5 | 1/5 |
| Shortness of breath | 1/5 | 0/5 |
| Decreased exercise tolerance | 5/5 | 1/5 |
| Sleep disturbance | 1/5 | 0/5 |
| Side Effects | | |
| Local irritation | not applicable | 2/5 |
| Edema | not applicable | 1/5 |

TABLE II

Routine Laboratory Studies Patients 1-5

| Day | Na⁺ | K⁺ | Cl | Bica | Bun | Cre | Ca | Pho | TP | Alb | Hct | Wbc |
|---|---|---|---|---|---|---|---|---|---|---|---|---|
| 0 | 139 | 3.6 | 101 | 22.8 | 69.8 | 6.5 | 9.9 | 5.6 | 7.0 | 3.9 | 31.1 | 8.0 |
| 3 | 138 | 3.7 | 99 | 23.2 | 63.2 | 6.3 | 9.5 | 5.9 | 6.2 | 3.5 | 30.2 | 8.2 |
| 24 | 139 | 4.0 | 102 | 22.6 | 57.5 | 5.9 | 9.8 | 5.3 | 6.8 | 3.8 | 28.6 | 8.1 |

$Na^+$ = Sodium
$K^+$ = Potassium
Cl = Chloride
Bica = Bicarbonate
Bun = Blood urea nitrogen
Cre = Creatinine
Ca = Calcium
Pho = Phosphorus
TP = Total protein
Alb = Albumin
Hct = Hematocrit
Wbc = White blood cell count

TABLE III

| | Day | | | | | | | |
|---|---|---|---|---|---|---|---|---|
| | 0 | 3 | 7 | 10 | 14 | 17 | 21 | 24 |
| Inulin Clearance | 7.7 | 10.8 | 10.2 | 9.8 | 10.9 | 13.9 | 11.4 | 12.0 |
| Std. error | 0.8 | 0.8 | 0.9 | 0.7 | 0.9 | 1.1 | 0.5 | 1.1 |
| PAH Clearance | 48.9 | 53.4 | 58.4 | 51.7 | 54.8 | 53.9 | 54.6 | 60.6 |
| Std. error | 10.4 | 15.2 | 11.0 | 12.6 | 15.4 | 13.9 | 13.4 | 16.6 |
| IGF-I Level | 170.8 | 291.8 | 153.5 | 338.4 | 144.4 | 276.5 | 137.8 | 303.8 |
| Std. error | 22.2 | 63.3 | 20.7 | 71.7 | 15.0 | 46.7 | 7.9 | 19.9 |
| BP-1 Level | 26.3 | 79.5 | 79.8 | 83.8 | 50.9 | 77.5 | 54.4 | 45.9 |
| Std. error | 6.1 | 53.7 | 41.5 | 40.3 | 23.7 | 54.2 | 29.8 | 20.7 |
| BP-2 Level | 2004.5 | 2570.5 | 1803.0 | 2701.0 | 1749.8 | 2256.3 | 1888.8 | 2326.4 |
| Std. error | 809.1 | 1160.7 | 762.9 | 823.7 | 606.2 | 604.3 | 636.0 | 551.1 |
| BP-3 Level | 3.7 | 3.5 | 4.1 | 4.0 | 3.6 | 3.4 | 3.7 | 3.8 |
| Std. error | 0.2 | 0.2 | 0.3 | 0.2 | 0.2 | 0.1 | 0.4 | 0.2 |

Summary and Conclusion

IGF-I can be administered safely in an intermittent fashion to patients with symptomatic ESRD. The treatment resulted in a sustained improvement in renal function over a 4-week period with resolution of most uremic symptoms. No adverse side effects were observed in patients receiving the IGF-I in an intermittent mode. The improvement in renal function persisted throughout the administration cycle despite IGF-I levels returning to baseline after each period of intermittent exposure and prior to the next treatment cycle. Administration of IGF-I in an intermittent manner did not suppress IGFBP3 levels over the course of four weeks.

Hence, administration of IGF-I in an intermittent fashion to patients with symptomatic ESRD can delay or obviate the need for dialysis or transplantation.

EXAMPLE II

Control Study A

The loss of lean body mass accompanying AIDS-associated cachexia is refractory to current modes of therapy. Ten subjects with AIDS-associated cachexia with an average weight loss of 15.8±2.1% (range 8.3–24.8%) were infused intravenously with low (4 µg/kg/hr) or high (12 µg/kg/hr) doses of recombinant human IGF-I formulated in citrate buffer as described in Example I for 12 hours each day over a period of 10 days following dietary stabilization. (This translates to an IGF-I dose of 48 or 144 µg/kg/day, respectively.) Protein turnover ($^{13}$C-leucine and $^{15}$N-glycine techniques) was measured as follows: $^{13}$C-leucine was infused on days −1 and 10. Twenty-four-hour infusions of $^{15}$N-glycine were performed on days −2 and 9. Nitrogen balance was measured at baseline and during the final three days of IGF-I administration. Nitrogen retention was followed throughout IGF-I infusion.

Cumulative nitrogen retention was significantly positive during the first seven days of treatment (+9.52±4.09 g, p<0.05), but the effect was transient. Nitrogen balance and indices of protein turnover during the final three days of treatment were unchanged compared to baseline. There was a trend toward lower (1.32±0.82 g/day vs. 3.24±1.19 g/day) and earlier (median day 6 vs. median day 10) peak nitrogen retention with high-dose than with low-dose IGF-I infusion. With repeated IGF-I administration, pre-infusion IGF-I levels increased (low dose: day 1, 151±23; day 5, 253±55; day 10, 249±51 µg/L; p=0.02; high dose: day 1, 124±16; day 5, 222±26; day 10, 179±28 µg/L; p=0.02), but the increment in circulating IGF-I during infusion decreased (low dose: day 1, 284±77; day 5, 132±55; day 10, 64±7 µg/L; p=0.08; high dose: day 1, 376±42; day 5, 249±38; day 10, 256±38 µg/L; p<0.01), producing a trend toward lower steady-state IGF-I levels. This was accompanied by declining levels of IGFBP3 (day 1, 3.09±0.21; day 5, 2.77±0.27; day 10, 2.57±0.20 mg/L; p=0.0003 for all 10 subjects together). Levels of IGFBP1 and IGFBP2 were also significantly affected by repeated IGF-I administration.

Hence, IGF-I promotes anabolism but tachyphylaxis develops rapidly. This is reported by Lieberman et al. (1993 and 1994), supra.

Control Study B

In this study, the utility of IGF-I was examined immobilized patients with severe head injuries, a condition associated with profound hypercatabolism and nitrogen loss. Within 72 hours of injury, male and female patients (n=24, 18–46 years) were randomized into two groups, receiving either an IV infusion of 0.01 mg/kg/hr recombinant human IGF-I in citrate buffer as described in Example I or saline for 14 days. Serum glucose concentrations and nitrogen balance were determined on every day of treatment. The interrelationships of free and total IGF-I with IGFBP2 and −3, and with other hormones, particularly insulin and GH, were established by measuring the plasma concentrations in samples collected prior to, during, and immediately after the infusions. In the majority of patients, free IGF-I was not measurable (<6.25 µg/L) at any time point. Glucose and insulin concentrations were comparable between the two groups throughout the study.

In the 11 saline-treated patients, mean (±SE) total IGF-I was 93±13 µg/L at pre-treatment, and the patients were in negative nitrogen balance (−2.9 g/day nitrogen) during the first week. As the patients recovered, total IGF-I increased to 144±29 µg/L by day 14, approaching endogenous levels in healthy adults (~200 µg/L). This increase in IGF-I did not occur until day 8 of treatment and was not associated with changes in IGFBP3, IGFBP2, or GH. However, during the second week of treatment, the saline-treated patients lost an average of 5.0 g/day nitrogen. Total IGF-I in the 13 patients on IGF-I increased from 78±14 to 466±40 µg/L by day 2. In contrast to the saline-treated group, the IGF-I-treated patients retained 1.3 g/day nitrogen for the first week. The IGF-I-treated patients only maintained total IGF-I steady state for 2 days; then IGF-I declined to 220±31 µg/L by day 14 prior to discontinuing therapy. This decline was associated with a decrease in IGFBP3 from 2.8±0.2 to 2.1±0.2 mg/L, and an increase in IGFBP2 from 275±46 to 678±145 µg/L over the 14-day period. Plasma concentrations of GH declined from 2.3±0.6 to a nadir of 0.4±0.1 µg/L on day 10 of IGF-I treatment. Furthermore, the IGF-i-treated patients lost an average of 4.9 g/day nitrogen during the second week.

In conclusion, in this study to examine the utility of IGF-I in critically ill patients, infusion of IGF-I produced only a transient positive nitrogen balance in these patients with severe catabolism. In the first week the patients experienced a positive nitrogen balance, but during the second week, a negative nitrogen balance was observed. Infusion of IGF-I led to the suppression of GH and IGFBP3, and to increases in IGFBP2, resulting in enhanced clearance of total IGF-I. This study is described by Chen et al., supra.

Intermittent Dosing

These two studies show that for 7 days of IGF-I treatment an anabolic effect was observed which subsided after 7 days. From these results it would be expected that the maximum period of treatment using IGF-I for anabolic response would be 7 days, followed by a rest from treatment of up to 7 days. Hence, when these two type of patients are treated identically as described, except that after 7 days of treatment with IGF-I they are not treated for from 2 to 7 days, they are expected to sustain a positive anabolic effect without tachyphylaxis.

EXAMPLE III

Seven patients with type II diabetes were injected subcutaneously with a dose of 120–160 µg/kg twice daily with recombinant human IGF-I obtained from Chiron Corp. for 4–52 days, as described by Jabri et al., supra. Four patients exhibited comparable or enhanced, whereas three had diminished, blood glucose control when treated with IGF-I relative to that while treated twice daily with NPH insulin during the six-week control period. The occurrence of adverse side effects in all patients compelled the authors to discontinue IGF-I administration before completing the 8-week treatment period. These adverse effects included edema, mild weight gain, occasional dyspnea, bilateral jaw tenderness, arthralgias and myalgias, fatigue, tachycardia, flushing, orthostatic hypotension, and local burning at the injection site. The authors concluded that the frequency and severity of side effects associated with administering high-dose subcutaneous IGF-I continuously to obese insulin-resistant diabetic patients made it an unacceptable therapeutic agent for these patients despite its ability to produce reasonable blood glucose control in about 50% of them.

It is expected that if the same patients are treated with IGF-I under the same conditions, but using intermittent dosing (3–12 days treatment, 2–10 days off treatment, 3–12 days treatment, etc., where the off-treatment period chosen is no longer than the on-treatment period utilized), their glucose levels will be lowered without the side effects observed.

What is claimed is:

1. A method for administering insulin-like growth factor-I (IGF-I) to a mammal so as to sustain its biological response in the treatment of a chronic disorder in the mammal comprising administering a therapeutically effective amount of IGF-I to the mammal to provide an exposure to IGF-I for a period of time that provides the maximum biological response in the mammal, then discontinuing said administration for a period of time equal to or less than the time period during which the IGF-I was previously administered, then administering a therapeutically effective amount of IGF-I to the mammal to provide an exposure to IGF-I for a period of time that provides the maximum biological response in the mammal, then discontinuing said administration for a period of time equal to or less than the time period during which the IGF-I was just previously administered, and repeating this pattern of administration and discontinuance of administration for as long as necessary to achieve or maintain sustained biological response in the mammal.

2. The method of claim 1 wherein the mammal is a human.

3. The method of claim 1 wherein the chronic disorder is chronic renal failure.

4. The method of claim 1 wherein the chronic disorder is diabetes.

5. The method of claim 1 wherein the chronic disorder is an anabolic disorder.

6. The method of claim 1 wherein the chronic disorder is a neurological, cardiac, or immunological disorder.

7. The method of claim 1 wherein when the IGF-I is administered, it is administered at least once a day consecutively.

8. The method of claim 1 wherein when the IGF-I is administered, it is administered in a long-acting formulation.

9. The method of claim 1 wherein the period that provides maximum biological response in the mammal is from about three to five days and the period of discontinuance of treatment of the mammal is from about two to four days.

10. The method of claim 1 wherein the period that provides maximum biological response in the mammal is from about seven to twelve days and the period of discontinuance of treatment of the mammal is from about two to seven days.

11. The method of claim 1 further comprising administering another drug to the mammal during the course of treatment.

12. The method of claim 11 wherein the drug is growth hormone.

13. The method of claim 11 wherein the drug is atrial natriuretic peptide.

14. The method of claim 11 wherein the drug is an ACE inhibitor.

15. The method of claim 11 wherein the drug is an IGF-I binding protein or acid-labile subunit.

16. The method of claim 1 wherein the IGF-I is complexed with an IGF binding protein or acid-labile subunit.

17. The method of claim 1 wherein the IGF-I is administered subcutaneously or intravenously.

* * * * *